(12) United States Patent
He et al.

(10) Patent No.: US 9,052,291 B2
(45) Date of Patent: Jun. 9, 2015

(54) OPTICAL SENSOR BASED ON A BROADBAND LIGHT SOURCE AND CASCADED WAVEGUIDE FILTERS

(75) Inventors: Jian-Jun He, Hangzhou (CN); Lei Jin, Hangzhou (CN); Mingyu Li, Hangzhou (CN)

(73) Assignee: Zhejiang University, Hangzhou (CN)

( * ) Notice: Subject to any disclaimer, the term of this patent is extended or adjusted under 35 U.S.C. 154(b) by 360 days.

(21) Appl. No.: 13/575,602

(22) PCT Filed: Jan. 21, 2011

(86) PCT No.: PCT/CN2011/070449
§ 371 (c)(1),
(2), (4) Date: Jul. 26, 2012

(87) PCT Pub. No.: WO2011/091735
PCT Pub. Date: Aug. 4, 2011

(65) Prior Publication Data
US 2012/0298849 A1  Nov. 29, 2012

(30) Foreign Application Priority Data

Jan. 29, 2010 (CN) .......................... 2010 1 0104762
Jun. 8, 2010 (CN) .......................... 2010 1 0195899

(51) Int. Cl.
*H01P 7/00* (2006.01)
*G01D 5/353* (2006.01)
*G01K 11/00* (2006.01)
*G01N 21/77* (2006.01)
*H01P 11/00* (2006.01)
*G01J 1/04* (2006.01)

(52) U.S. Cl.
CPC .......... *G01N 21/7746* (2013.01); *H01P 11/007* (2013.01); *H01P 7/00* (2013.01); *H01P 11/008* (2013.01); *H01P 11/00* (2013.01); *G01J 1/04* (2013.01); *G01D 5/35319* (2013.01); *G01K 11/00* (2013.01)

(58) Field of Classification Search
CPC ........... G01N 1/00; G01N 7/00; G01N 21/00; G01N 27/00; G01N 21/7746; G02B 26/00; G02B 6/00; H01P 7/00; H01P 11/00; H01P 11/008; H01P 11/007; G01D 5/35322; G01D 5/35329; G01D 5/35319; G01K 11/00; G01J 1/04
USPC ............. 250/227.14, 227.17, 227.18, 227.19, 250/227.24, 227.27, 227.28; 385/9, 10, 12, 385/15, 27, 28, 30, 31, 32, 37
See application file for complete search history.

(56) References Cited

U.S. PATENT DOCUMENTS 7,065,276 B2 *   6/2006  Scheuer et al. .................. 385/50
7,525,461 B1 *   4/2009  Uhlhorn ........................ 341/137
7,796,262 B1 *   9/2010  Wang et al. .................... 356/436

*Primary Examiner* — Georgia Y Epps
*Assistant Examiner* — Don Williams
(74) *Attorney, Agent, or Firm* — Lightip Technologies

(57) ABSTRACT

An optical sensor based on a broadband light source and cascaded waveguide filters comprises a broadband light source, an input waveguide, a reference ring resonator coupled with the input waveguide, a common bus waveguide coupled with the reference ring resonator, a sensing ring resonator coupled with the common bus waveguide, an output waveguide coupled with the sensing ring resonator, and two optical power detectors. At least a portion of the sensing ring resonator is influenced by the physical parameter to be measured or in contact with an analyte. The variation of the physical parameter to be measured or the variation of the analyte induces a shift of the transmission spectrum of the sensing ring resonator. By using the cascaded filtering effect of the double resonators, the wavelength shift can be translated into a variation of the total output power. Consequently the physical parameter to be measured can be easily deduced.

16 Claims, 9 Drawing Sheets

OPTICAL SENSOR BASED ON A BROADBAND LIGHT SOURCE AND CASCADED WAVEGUIDE FILTERS

FIELD OF THE INVENTION

This invention relates generally to an optical waveguide sensor, more particularly to an optical waveguide sensor based on a broadband light source and cascaded optical waveguide filters or cascaded ring resonators.

BACKGROUND OF THE INVENTION

Optical sensing technology as an important branch of information science technology has important applications in the fields of industry process control, environment monitoring, food security and homeland security. Optical sensing technology can solve problems of electrical sensing technology such as low sensitivity, interference, slow, insecurity for some chemical gases. Optical sensor has advantages of high sensitivity, compact, immunity to electromagnetic interference, suitable for integration and real time measurements, playing a more and more important role in the sensing field.

The basic principle of optical waveguide sensor is based on evanescent filed at the surface of fiber or planar waveguides. The interaction between evanescent filed and the analyte will influence the transmission characteristics of the optical waveguide, thereby achieving optical sensing by detecting the change of the transmitted light.

Ring resonator has attracted considerable attentions because it can provide a high sensitivity due to its sharp resonance peak. FIG. 1 shows the schematic diagram of an optical sensor based on a single ring resonator. The variation of the effective refractive index induces a shift in the transmission spectrum of the ring resonator. By measuring the peak wavelength shift or intensity change at a fixed wavelength around one transmission peak, the change of the analyte can be detected (K. De Vos et al, "Silicon-on-Insulator microring resonator for sensitive and label-free biosensing", Optics Express 15, pp. 7610-7615, 2007). The drawback of the wavelength shift measurement is the need for an expensive optical spectrum analyzer (OSA), and the detection precision is directly related to the resolution of the OSA. In the case of measuring intensity at a fixed wavelength around a transmission peak, it needs a laser source with a narrow linewidth and an accurate wavelength relative to the position of the transmission peak, and a good stability. These requirements increase the cost of the measurement system, and decrease the reliability.

SUMMARY OF THE INVENTION

The objective of the present invention is to provide an optical sensor based on a broadband light source and cascaded optical waveguide filters, which uses low cost broadband light source such as light emitting diode (LED) as the input light source, and detects the analyte or the physical parameter to be measured by measuring the output power over the total spectrum without requiring the spectral information, and with much reduced requirements on the stability of the light source and the measurement system.

The present invention achieves the objective through the following technical implementations.

Implementation 1:

An optical sensor based on a broadband light source and cascaded waveguide filters comprising: a broadband light source, an input waveguide coupled with the broadband light source, a reference ring resonator coupled with the input waveguide, a common bus waveguide coupled with the reference ring resonator, a sensing ring resonator coupled with the common bus waveguide, an output waveguide coupled with the sensing ring resonator, an optical power detector coupled with the output waveguide for measuring the output power; the optical path lengths of said reference ring resonator and sensing ring resonator are substantially the same, the resonant frequencies of said reference ring resonator correspond to a series of equally spaced operation frequencies, the resonant frequencies of said sensing ring resonator coincide with the resonant frequencies of said reference ring resonator; at least a portion of the waveguide of the sensing ring resonator is effected by the physical parameter to be measured or is in contact with the analyte.

Said waveguides and ring resonators are coupled by directional couplers or multimode interference couplers.

Said broadband light source is a light emitting diode. The other end of said input waveguide is coupled with a second optical power detector.

Said physical parameter to be measured is stress or temperature, and said analyte is a liquid or a gas.

Implementation 2:

An optical sensor based on a broadband light source and cascaded waveguide filters comprising: a broadband light source, an input waveguide, a reference optical filter, a common bus waveguide, a sensing optical filter, an output waveguide, and an optical power detector, which are coupled in sequence; the transmission frequencies of said reference optical filter correspond to a series of equally spaced operation frequencies, the transmission frequencies of said sensing optical filter coincide with the transmission frequencies of said reference optical filter; at least a portion of the waveguide of the sensing optical filter is effected by the physical parameter to be measured or is in contact with the analyte.

Said waveguides and optical filters are comprised of fibers or planar integrated waveguides.

Said optical filters are comprised of one or several Mach-Zehnder interferometers, or array waveguide gratings, or Fabre-Perot interferometers.

Implementation 3:

An optical sensor based on a broadband light source and cascaded waveguide filters comprising: a broadband light source, an input waveguide coupled with the broadband light source, a reference ring resonator coupled with the input waveguide, a common bus waveguide coupled with the reference ring resonator, a sensing ring resonator coupled with the common bus waveguide, an output waveguide coupled with the sensing ring resonator, an optical power detector coupled with the output waveguide for measuring the output power; the optical path lengths of said reference ring resonator and sensing ring resonator are slightly different so that the resonant frequency of said reference ring resonator correspond to a series of equally spaced operation frequencies, and when one resonant frequency of said sensing ring resonator coincides with one resonant frequency of said reference ring resonator, the adjacent resonant peaks do not overlap completely; at least a portion of the waveguide of the sensing ring resonator is effected by the physical parameter to be measured or is in contact with the analyte.

Said couplers between the input waveguide, the common bus waveguide and the reference ring resonator are directional couplers or multimode interference couplers; said couplers between the output waveguide, the common bus waveguide and the sensing ring resonator are directional couplers or multimode interference couplers.

Said broadband light source is a light emitting diode.

The other end of said input waveguide is coupled with a second optical power detector.

Said physical parameter to be measured is stress or temperature, and said analyte is a liquid or a gas.

Implementation 4:

An optical sensor based on a broadband light source and cascaded waveguide filters comprising: a broadband light source, an input waveguide, a reference optical filter, a common bus waveguide, a sensing optical filter, an output waveguide, an optical power detector, which are coupled in sequence; the transmission frequency of said reference optical filter correspond to a series of equally spaced operation frequencies, and when one transmission frequency of said sensing optical filter coincides with one transmission frequency of said reference optical filter, the adjacent transmission peaks are not overlapped completely; at least a portion of the waveguide of the sensing optical filter is effected by the physical parameter to be measured or is in contact with the analyte.

Said input waveguide, the output waveguide, the common bus waveguide, the reference optical filter and the sensing optical filter are comprised of fibers or planar integrated waveguides.

Said reference optical filter and sensing optical filter are comprised of one or several Mach-Zehnder interferometers, or array waveguide gratings, or Fabre-Perot interferometers.

The present invention has benefits as follows:

(1) By using the filtering effect of two cascaded ring with the same cavity length, the shift of the sensing ring resonator spectrum is translated into simultaneous intensity change of all peaks over the entire transmission spectrum, and by measuring the output power of the overall spectrum to detect analyte or the physical parameter to be measured. A low cost broadband light source such as a light emitting diode is used as the input light source, without requiring an expensive tunable laser. What needs to be measured is only output power in the total spectrum. There is no need to measure wavelength or using a high resolution optical spectrum analyzer (OSA). Therefore, the cost is significantly reduced, making it suitable for practical use. Besides, the sensitivity is increased, and the detection limit can reach as small as $3.9 \times 10^{-7}$ RIU.

(2) By using Vernier effect of two cascaded ring with different cavity lengths, the shift of sensing ring resonator is translated into the envelope shift of the total transmission spectrum. By measuring the output power over the spectrum of a light source, the analyte content or the physical parameter to be measured can be derived. A low cost broadband light source such as a light emitting diode is used as the input light source, without requiring an expensive tunable laser. What needs to be measured is only output power in the total spectrum. There is no need to measure wavelength or using a high resolution optical spectrum analyzer (OSA). Therefore, the cost is significantly reduced, making it suitable for practical use. Besides, the sensitivity is increased, and the detection limit can reach as small as $6.5 \times 10^{-7}$ RIU.

Notations used in the figures: 0. broadband light source, 1. input waveguide, 2. output waveguide, 3. common bus waveguide, 10. reference ring resonator, 20. sensing ring resonator, 51. multimode interference coupler, 52. multimode interference coupler, 53. multimode interference coupler, 54. multimode interference coupler, 41. optical power detector, 42. optical power detector, 101. reference optical filter, 102. sensing optical filter.

DETAILED DESCRIPTION

In the following the present invention will be described in more detail with reference to the drawings and example embodiments.

The First Implementation of the Invention

Figure 1:
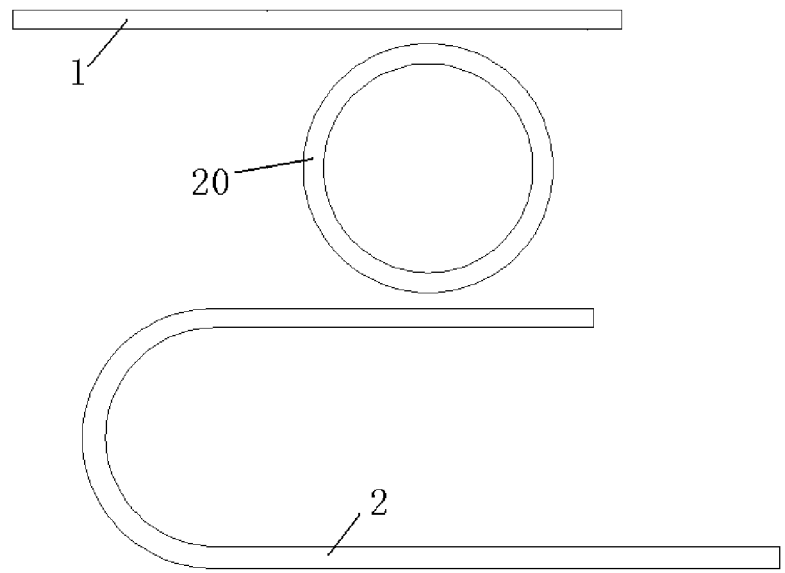
FIG. 1 is a schematic diagram of a prior-art optical waveguide sensor based on a single ring resonator.
Figure 2:
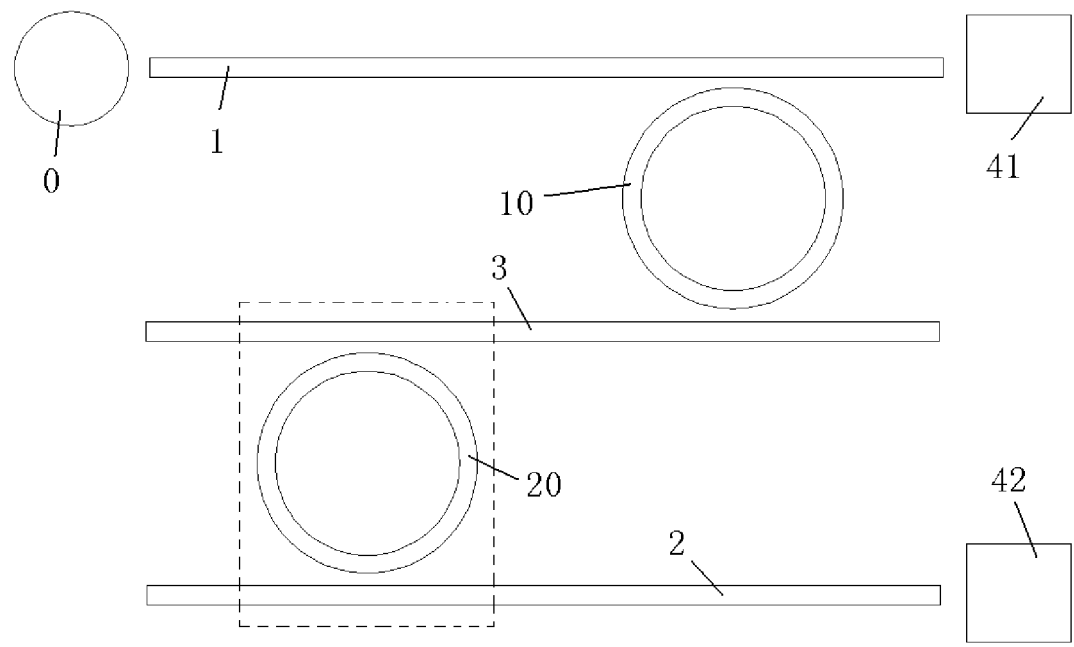
FIG. 2 is a schematic diagram of the first implementation of the present invention.

FIG. 2 is the first implementation of the present invention. It consists of a broadband light source 0, an input waveguide 1 coupled with the broadband light source 0, a reference ring resonator 10 coupled with the input waveguide, a common bus waveguide 3 coupled with the reference ring resonator 10, a sensing ring resonator 20 coupled with the common bus waveguide 3, an output waveguide 2 coupled with the sensing ring resonator 20, an optical power detector 42 coupled with the output waveguide 2 for measuring the output power, the optical lengths of the reference ring resonator and the sensing ring resonator are substantially the same. The resonant frequency of the reference ring resonator 10 corresponds to a series of equally spaced operation frequencies, and the resonant frequencies of the sensing ring resonator 20 coincide with the resonant frequencies of the reference ring resonator 10. At least a portion of the sensing ring resonator 20 (e.g. within the dashed-line rectangle) is effected by the physical parameter to be measured such as stress or temperature, or is in contact with an analyte. The change of the physical parameter such as the stress or temperature will influence the optical length of the sensing ring resonator 20, or, the refractive index variation of the analyte will influence the optical length of the sensing ring resonator 20 through the evanescent field interaction. This consequently results in a shift of the resonant peaks. Through the cascaded filtering effect of the two resonators, the shift is translated into highly-sensitive simultaneous intensity change of all peaks in the entire transmission spectrum. By measuring the output power from output waveguide 2 using power detector 42, the physical parameter to be measured or the information such as the refractive index and concentration of the analyte can be derived. Power detector 41 is used to measure power from the through port of input waveguide 1 (a constant value close to the power of the light source). The power measured from detector 42 can be normalized by the power measured from detector 41 to eliminate the influence of the fluctuation of the input power.

The couplers between the waveguides and the ring resonators are implemented as directional couplers in this example.

The light from broadband light source 0 enters input waveguide 1, and propagates towards the right to the coupling region between waveguide 1 and reference ring resonator 10. Some of the light is coupled into the ring, and begin to resonate. Due to the self interference, only if the optical path length (the product of length and the effective index) of reference ring resonator 10 is an integer multiple of the wavelength, the light can be coupled into the common bus waveguide and propagate towards the left. The remaining of the light will exit from the other end of the input waveguide on the right. For the same reason, only if the resonant condition of the sensing ring resonator 20 is satisfied, the light in the common bus waveguide 3 can be coupled into the output waveguide 2 though the sensing ring resonator 20, and exit to the output port.

The amplitude transmission coefficient of a ring resonator is given by $$t = \frac{-c^2 e^{jk_0 n\pi R}}{1-(1-c^2)e^{2jk_0 n\pi R}} \quad (1)$$

where c is the coupling coefficient between the ring and the waveguide, n and R are the effective index and radius of the ring, respectively. $k_0$ is the wave number in vacuum. From equation (1), we can obtain the resonant condition:

$$2n\pi R = m\lambda \quad (2)$$

where λ is the wavelength and m is an integer.

Since the two rings have the same optical path length, their transmission spectra are the same (with the same free spectral range FSR). When they are cascaded, the total transmission spectrum is $$T=T_1 \times T_2 \quad (3)$$

where $T_1=|t_1|^2$, $T_2=|t_2|^2$ are the transmission spectra of the reference ring resonator 10 and the sensing ring resonator 20, respectively.

Figure 3:
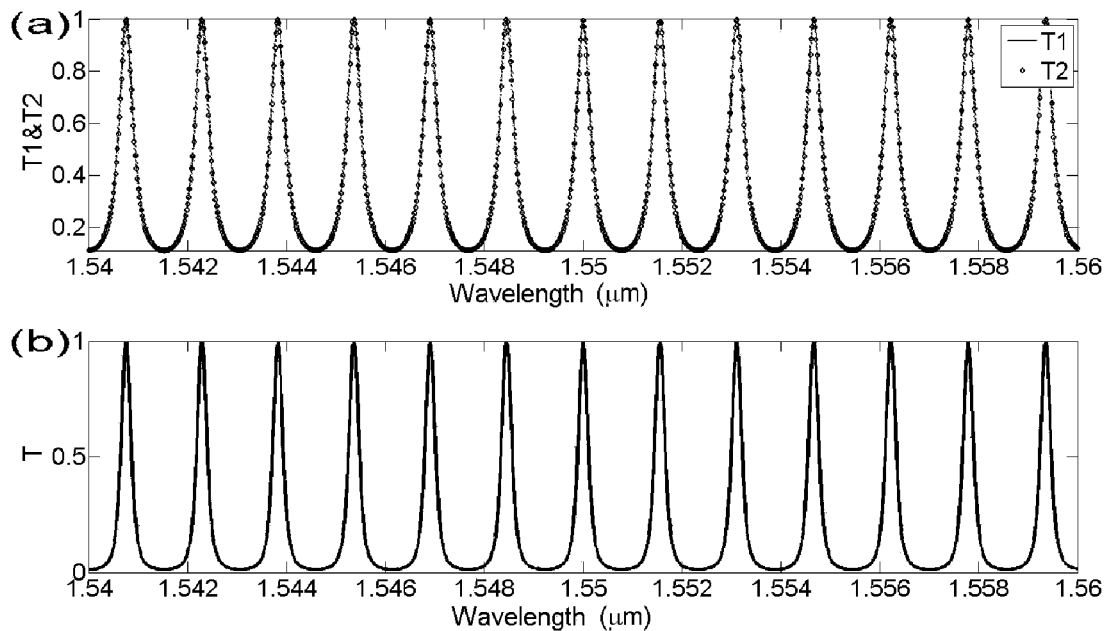
FIG. 3(a) and FIG. 3(b) are schematic diagrams of the transmission spectrum of the first implementation of the present invention.

FIG. 3 shows the transmission spectra of the reference ring resonator 10 and the sensing ring resonator 20(a), and the total transmission spectrum (b) in the first implementation of the present invention. For the resonant wavelengths of the reference ring resonator 10, the sensing ring resonator 20 also resonates. The total transmission therefore reaches the maximum.

The optical path length of the sensing ring resonator 20 can change with some physical parameters such the stress and temperature. It can also change when the refractive index of the analyte changes, due to the evanescent field coupling. We have $$\frac{d\lambda}{\lambda} = \frac{dL}{L}(L = 2n\pi R \text{ is the optical path length}) \quad (4)$$

Figure 4:
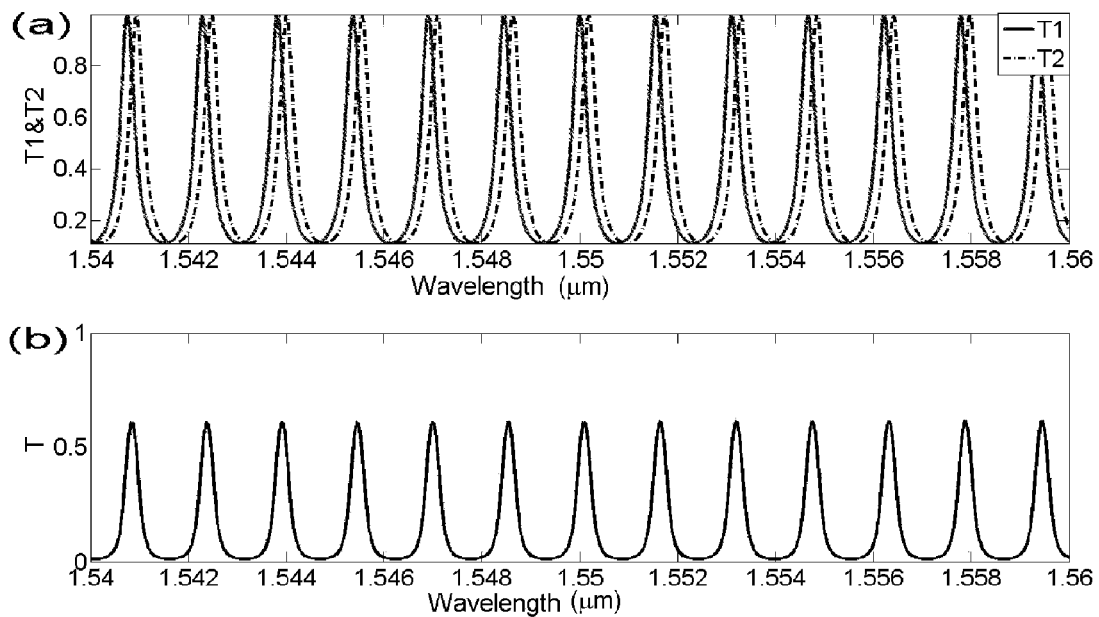
FIG. 4(a) and FIG. 4(b) are schematic diagrams of the transmission spectrum of the first implementation of the present invention after the analyte changes.

Accordingly, the transmission spectrum $T_2$ of the sensing ring resonator 20 will shift. As shown in FIG. 4(a), the transmission peaks of $T_1$ and $T_2$ undergo a relative displacement, resulting in a reduction in the total transmission spectrum of all peaks, as shown in FIG. 4(b).

Figure 5:
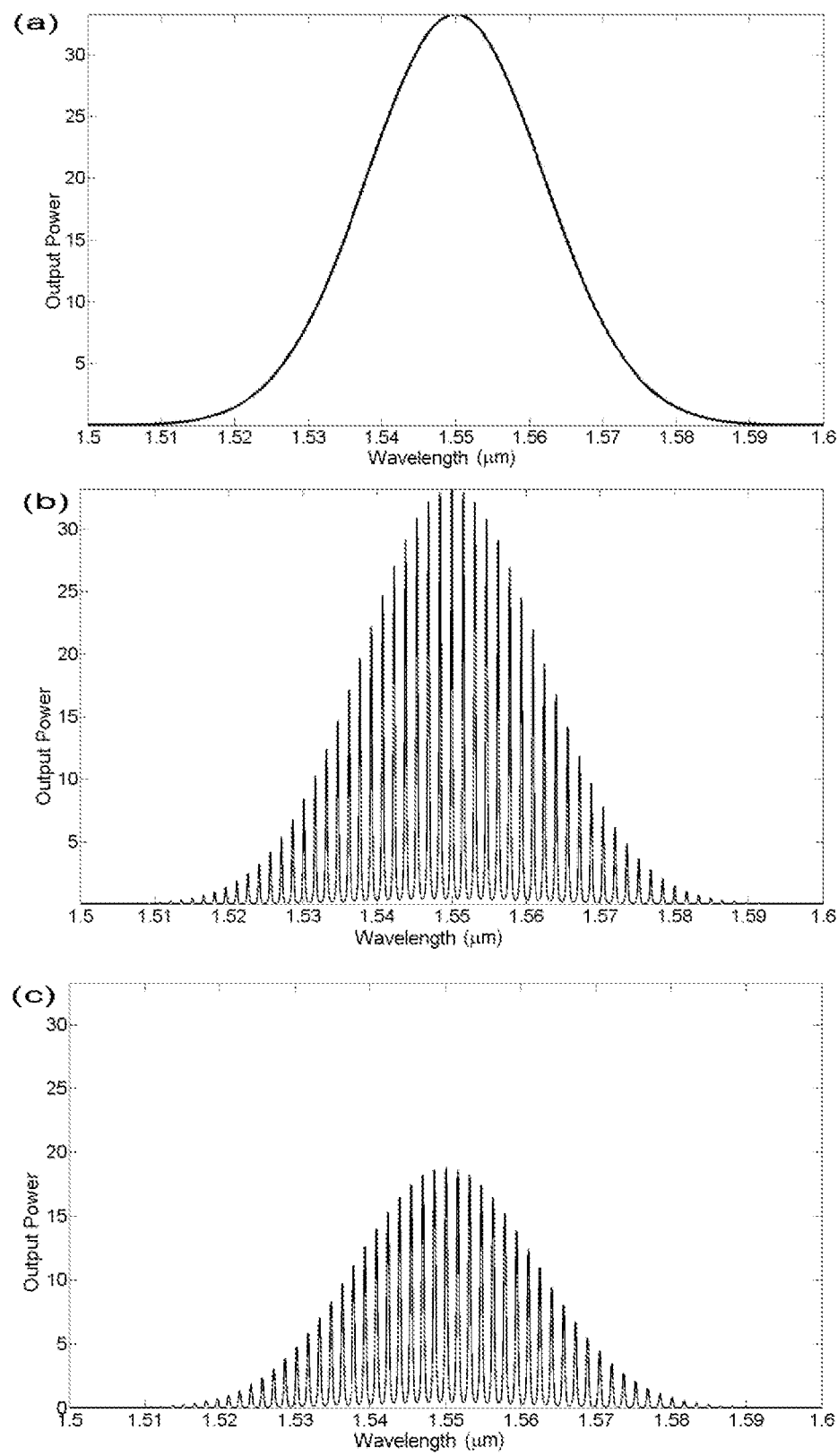
FIG. 5 (a) is the representative spectrum of a LED light source, (b) is the total output spectrum using LED light source in the first implementation of the present invention, (c) is the total output spectrum using LED light source in the first implementation of the present invention after the analyte changes.

When an LED is used as the broadband light source which has a spectrum as illustrated in FIG. 5(a), the total output spectra will appear as shown in FIGS. 5(b) and 5(c) before and after $T_2$ shifts. The physical parameter to be measured or the analyte content can then be detected by measuring the output power of the total spectrum.

Considering an example of a strip waveguide of 1 μm wide and 0.22 μm thick based on SOI (silicon-on-insulator) platform with a core refractive index of 3.48 and a lower-cladding index of 1.444. For TM polarization mode, the ratio between the change of the mode effective index $n_{eff}$ and the change of the upper-cladding index $n_c$ is:

$$\delta\delta= \quad (5)$$

For TE mode, the ratio between the change of the mode effective index $n_{eff}$ and the change of the upper cladding index $n_c$ is:

$$\delta\delta= \quad (6)$$

Figure 6:
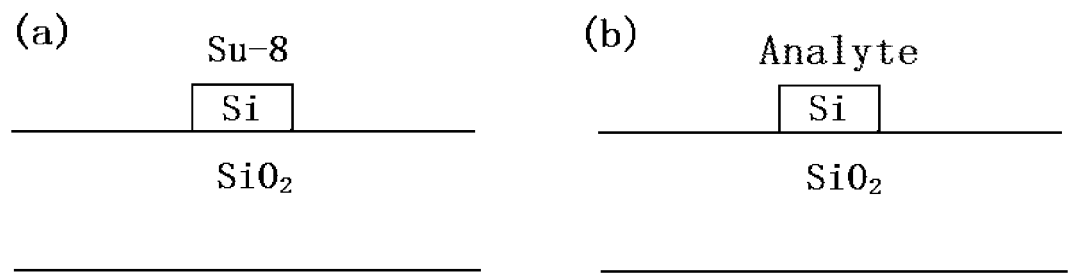
FIG. 6(a) and FIG. 6(b) are cross sections of the non-sensing waveguide and the sensing waveguide.

FIG. 6 gives the cross-sections of the waveguides of the sensor. (a) gives the cross-section of non-sensing waveguide, where Su-8 polymer, silicon oxide, or a material with similar refractive index as the analyte can be used as the upper cladding, which also provides protection of the waveguide from contacting the analyte. (b) gives the cross-section of the waveguide in the sensing section, where the cladding is analyte to be measured whose refractive index variation induces a change of the effective index of the waveguide.

As a numerical example, the radius of the two rings is 140 μm, the energy coupling efficiency is assumed to be 10%, and the loss of waveguide is 1 dB/cm, and the power of the LED light source is set to be 1 mW.

Figure 7:
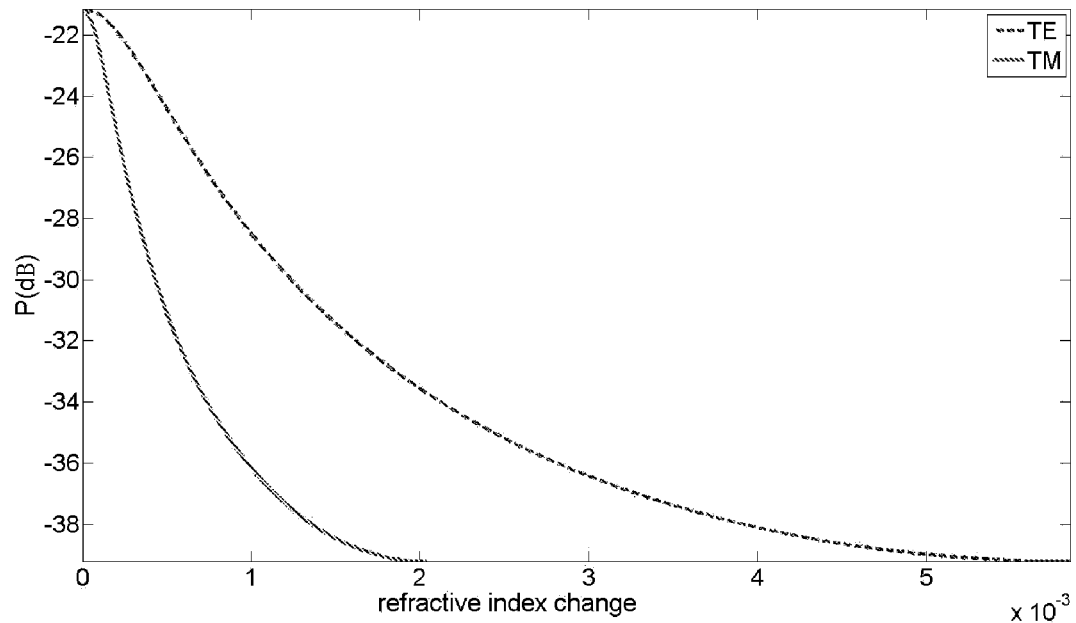
FIG. 7 is total output power change using TM mode and TE mode in the first implementation of the present invention.

FIG. 7 gives the total output power change for TM mode when the refractive index of the analyte changes from 1.33 to $1.33+2.02\times10^{-3}$, and for TE mode when the refractive index of the analyte changes from 1.33 to $1.33+5.84\times10^{-3}$. As we can see, when the refractive index of the analyte changes, the total output power decreases because of the increasing displacement of resonant peaks between $T_1$ and $T_2$. According to our calculation results, the highest sensitivity for TM mode reaches 25600 dB/RIU. Assuming that the power measurement accuracy is 0.01 dB, a refractive index variation as small as $3.9\times10^{-7}$ can be detected. The highest sensitivity for TE mode reaches 8700 dB/RIU. The corresponding detection limit of the refractive index variation is $1.15\times10^{-6}$.

The sensitivities for TE and TM mode are different because the ratios between the change of the effective index $n_{eff}$ and the change of the upper cladding index $n_c$ are different, and also the waveguide mode dispersions are different. The sensitivity of TM mode is higher with a smaller measurement range, while the sensitivity of TE mode is lower with a larger measurement range. In practice, one can use a polarization splitter to divide the two polarizations of the LED light into two separate cascaded-double-ring sensors, forming two detection channels. One can choose any one for use according to the required detection sensitivity and measurement range, or combine both to achieve a high sensitivity and a large measurement range at the same time.

The Second Implementation of the Invention

Figure 8:
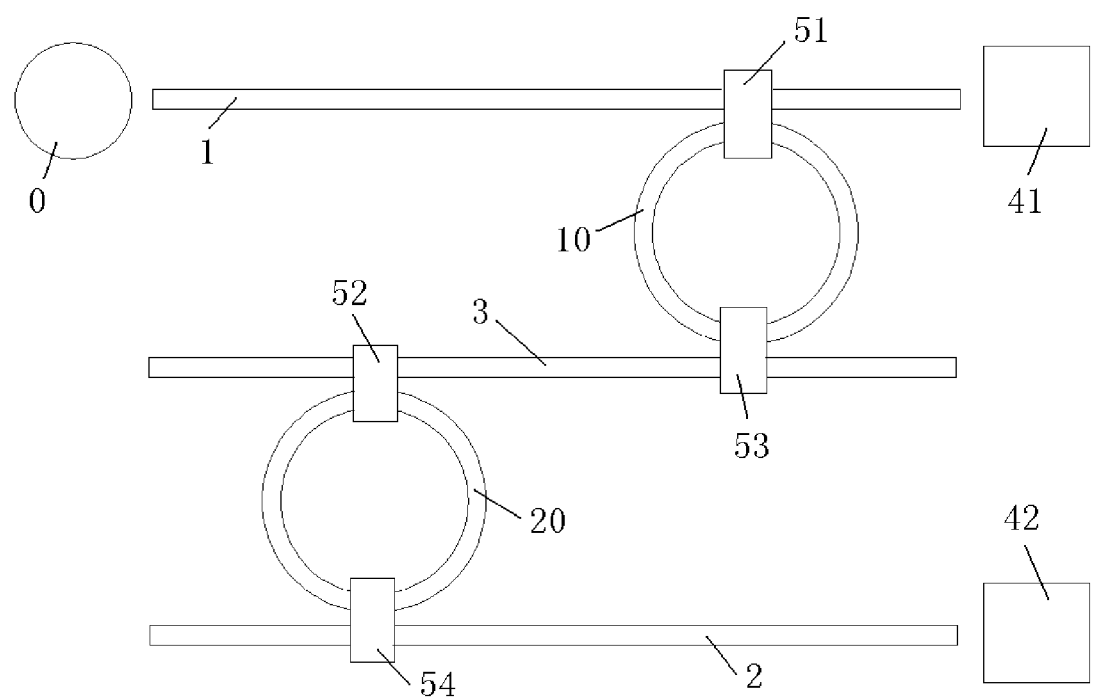
FIG. 8 is a schematic diagram of the second implementation of the present invention.

FIG. 8 is the second implementation of the present invention. It consists of a broadband light source 0, an input waveguide 1 coupled with the broadband light source 0, a reference ring resonator 10 coupled with the input waveguide, a common bus waveguide 3 coupled with the reference ring resonator 10, a sensing ring resonator 20 coupled with the common bus waveguide 3, an output waveguide 2 coupled with the sensing ring resonator 20, an optical power detector 42 coupled with the output waveguide 2 for measuring the output power. The optical lengths of the reference ring resonator and the sensing ring resonator are the same. The resonant frequencies of the reference ring resonator 10 correspond to a series of equally spaced operation frequencies, and the resonant frequencies of the sensing ring resonator 20 coincide with the resonant frequencies of the reference ring resonator 10. At least a portion of the sensing ring resonator 20 is the sensing section (e.g. in the dashed-line rectangle) which is effected by the physical parameter to be measured such as the stress or temperature, or in contact with an analyte to be measured. The change of the physical parameter such as the stress or temperature will influence the optical path length of the sensing ring resonator 20. Or, the change of the refractive index of the analyte will influence the optical path length of the sensing ring resonator 20 because of the evanescent field coupling, which consequently induces a shift of resonant peaks. Through the cascaded filter effect of the two resonators, the shift is translated into highly-sensitive simultaneous intensity change of all peaks in the total transmission spectrum. According to the output power measured from the output waveguide 2 using power detector 42, the physical parameter to be measured or the analyte information such as refractive index and concentration can be detected. The power detector 41 is used to measure power from the through-port of input waveguide 1 (a constant value close to the power of the light source). The power of power detector 42 can be normalized by the power detector 41 to eliminate the influence of the fluctuation of the input power.

In FIG. 8, the waveguides and ring resonators are coupled by multimode interference coupler 51, 52, 53, and 54.

The implementations above mainly concern the situations when the waveguides and ring resonators are based on planar waveguides. The waveguides and ring resonators also can be based on fibers or nano fibers, and the coupling can be realized by fusing or evanescent field coupling. The fiber has an advantage of polarization-insensitivity. The micro-ring based on nano fiber can increase the spacing between the resonant peaks, increasing the relative tolerance of ring length.

The Third Implementation of the Invention

The ring resonators in the above embodiments of the invention is used as optical filters. They have advantages of high quality factor (Q-factor). However, the ring resonators can be replaced by other filters such as Mach-Zehnder interferometers or array waveguide gratings or Fabre-Perot interferometers. The Fabre-Perot interferometer can consist of two Bragg gratings.

Figure 9:
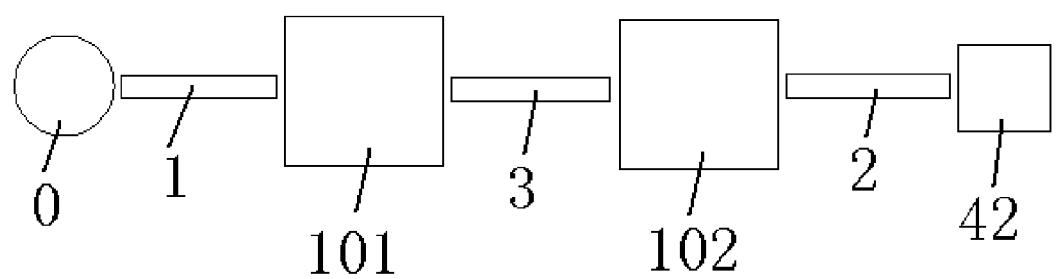
FIG. 9 is a schematic diagram of the third implementation of the present invention.

As shown in FIG. 9, the sensor consists of a broadband light source 0, an input waveguide 1 coupled with the broadband light source, a reference optical filter 101 coupled with the input waveguide, a common bus waveguide 3 coupled with the reference optical filter 101, a sensing optical filter 102 coupled with the common bus waveguide 3, an output waveguide 2 coupled with the sensing optical filter 102, an optical power detector 42 used for measuring output power. The transmission frequencies of the reference optical filter 101 correspond to a series of equally spaced operation frequencies, and the transmission frequencies of the sensing optical filter 102 coincide with the transmission frequencies of the reference optical filter 101. At least a portion of the sensing optical filter 102 is influenced by the physical parameter to be measured such as the stress or temperature, or is in contact with the analyte. The change of the physical parameter such as the stress or temperature will change the transmission frequencies of sensing optical filter 102. Through the cascaded filtering effect of the two optical filters, the change of the transmission frequencies is translated into highly-sensitive simultaneous intensity change of all peaks in the total transmission spectrum. According to the output power measured from output waveguide 2 using power detector 42, the physical parameter to be measured or the analyte information such as the refractive index and concentration can be detected.

The Fourth Implementation of the Invention

Figure 10:
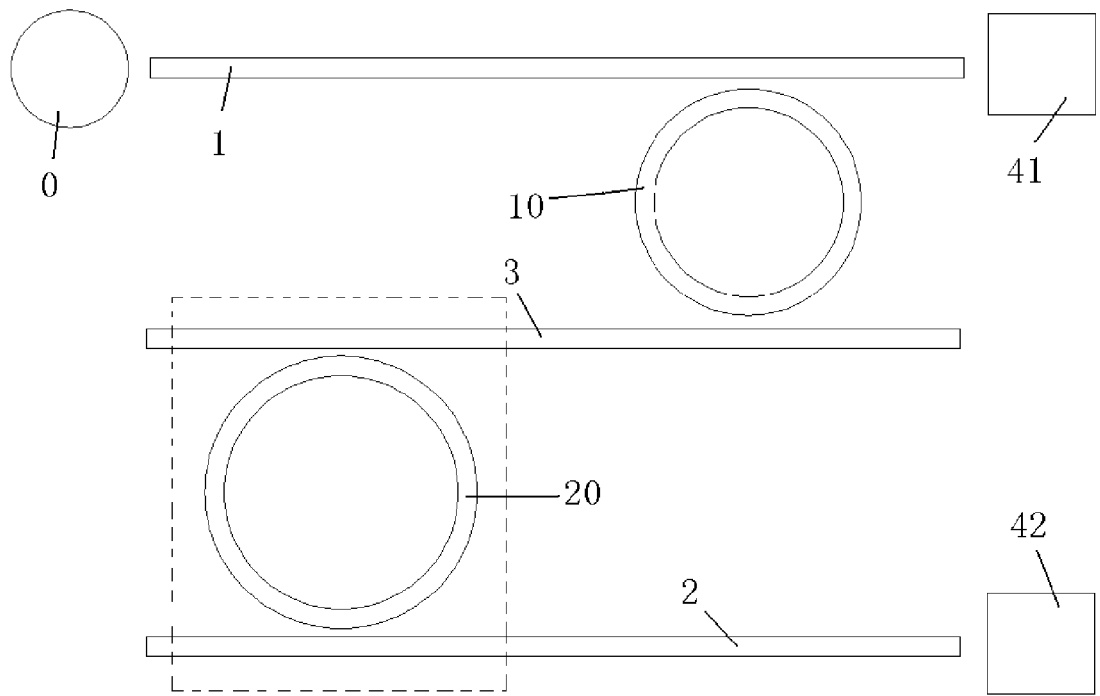
FIG. 10 is a schematic diagram of the fourth implementation of the present invention.

FIG. 10 is the fourth implementation of the present invention. The sensor consists of a broadband light source 0, an input waveguide 1 coupled with the broadband light source 0, a reference ring resonator 10 coupled with the input waveguide, a common bus waveguide 3 coupled with the reference ring resonator 10, a sensing ring resonator 20 coupled with the common bus waveguide 3, an output waveguide 2 coupled with the sensing ring resonator 20, an optical power detector 42 coupled with the output waveguide 2 for measuring the output power. The optical path lengths of the reference ring resonator and the sensing ring resonator are different. The resonant frequencies of the reference ring resonator 10 correspond to a series of equally spaced operation frequencies. When one resonant frequency of the sensing ring resonator 20 coincides with one resonant frequency of the reference ring resonator 10, the adjacent resonant peaks are not completely overlapped. At least a portion of the sensing ring resonator 20 is the sensing section (e.g. in the dashed-line rectangle) which is influenced by the physical parameter to be measured such as the stress or temperature, or is in contact with the analyte. The change of the physical parameter such as the stress or temperature will influence the optical path length of the sensing ring resonator 20, or the change of the refractive index of the analyte will influence the optical path length of the sensing ring resonator 20 due to the evanescent field coupling. This consequently induces a shift of the resonant peaks. The shift is translated into an amplified shift of the envelope of the total transmission spectrum because of the Vernier effect of the cascaded rings. This results in a large displacement between the central wavelength of the total transmission spectrum and the central wavelength of the light source, and consequently a change in the total transmitted power. From the output power measured from output waveguide 2 using power detector 42, the physical parameter to be measured or the analyte information such as the refractive index and concentration can be derived. The power detector 41 is used to measure the power from the through-port of the input waveguide 1 (a constant value close to the power of the input light source). The power measure from the detector 42 can be normalized by the one measure from the detector 41 to eliminate the influence of the fluctuation of the input power.

The couplers between the waveguides and the ring resonators in the example of FIG. 10 are directional couplers.

The light from the broadband light source 0 enters into input waveguide 1, and then propagates towards the right to the coupling region between waveguide 1 and reference ring resonator 10. Some of the light will couple into the ring, and begin to resonate. Due to the self-interference, only if the optical path length (product of length and effective index) of the reference ring resonator 10 is an integer multiples of the wavelength, the light can be coupled into the common bus waveguide and propagate towards left, and the remaining of the light will exit from the other end of the input waveguide on the right. For the same reason, only if the resonant condition of the sensing ring resonator 20 is satisfied, the light in the common waveguide 3 can be coupled into the output waveguide 2 though the sensing ring resonator 20, and exits to the output.

The amplitude transmission coefficient of ring resonator is given in Eq. (1), and the resonant condition is given in Eq. (2). Because the optical path lengths of the two rings are different, their transmission spectra are also different (different free spectral range FSR).

Figure 11:
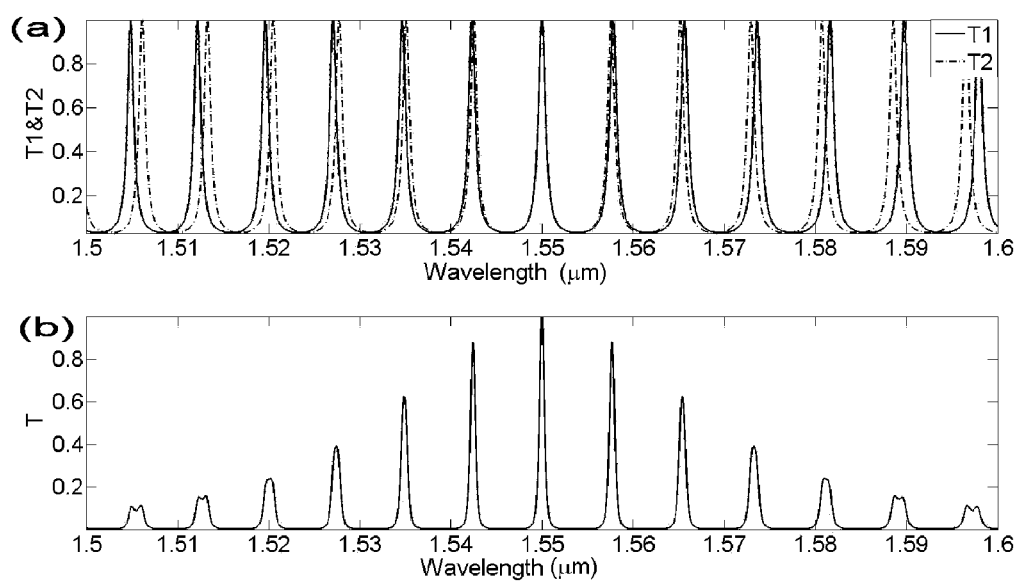
FIG. 11(a) and FIG. 11(b) are schematic diagrams of the transmission spectrum of the fourth implementation of the present invention.

FIG. 11(a) shows the transmission spectra of the reference ring resonator 10 and the sensing ring resonator 20 in the fourth implementation of the present invention, and FIG. 11(b) shows the total transmission spectrum calculated by Eq. (3). At the wavelength of 1550 nm, both rings resonate and the transmission reaches the maximum, which means 1550 nm is the initial central wavelength.

Figure 12:
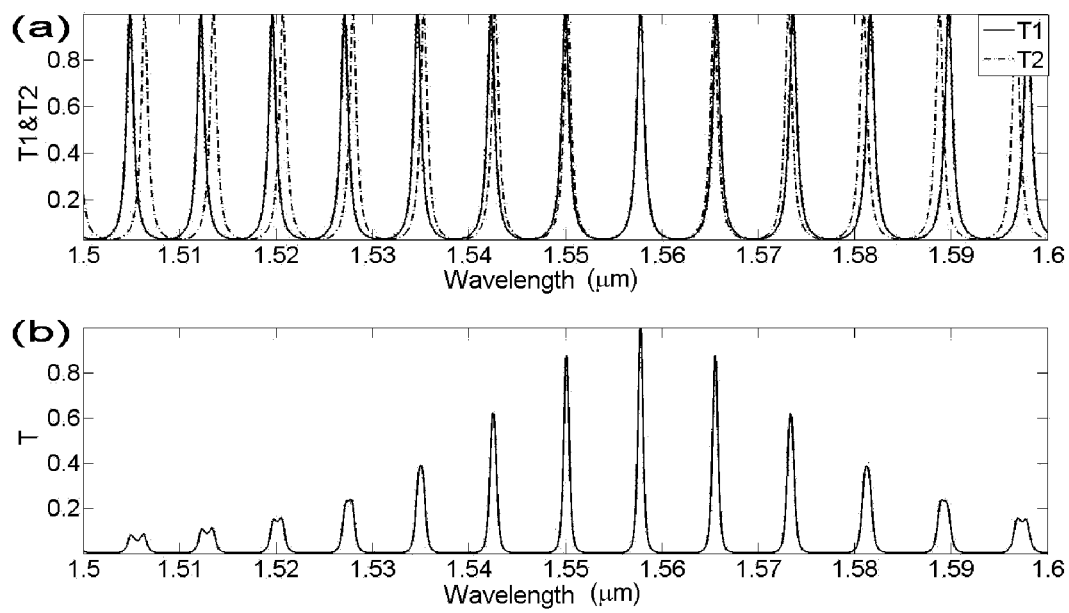
FIG. 12(a) and FIG. 12(b) are schematic diagrams of the transmission spectrum of the fourth implementation of the present invention after the analyte changes.

The change of the physical parameter such as the stress or temperature can influence the optical path length of the sensing ring resonator 20. The variation of the refractive index of the analyte can also influence the optical path length of the sensing ring resonator 20 through the evanescent field coupling. According to Eq. (4), the transmission spectrum of the sensing ring resonator 20 will shift. As shown in FIG. 12(a), at the wavelength of 1550 nm, the resonant frequencies of $T_1$ and $T_2$ no longer coincide, while their adjacent peaks become overlapped. FIG. 12(b) shows that the envelope function of the total transmission spectrum shifts and the central wavelength moves to the adjacent peak. As we can see, when $T_2$ shifts by $FSR_1-FSR_2$, the central wavelength shifts by $FSR_1$, which means the shift of $T_2$ is amplified by a factor of $FSR_1/|FSR_1-FSR_2|$, this is the so called Vernier effect (here $FSR_1$, $FSR_2$ are free spectral range of $T_1$ and $T_2$, respectively).

Figure 13:
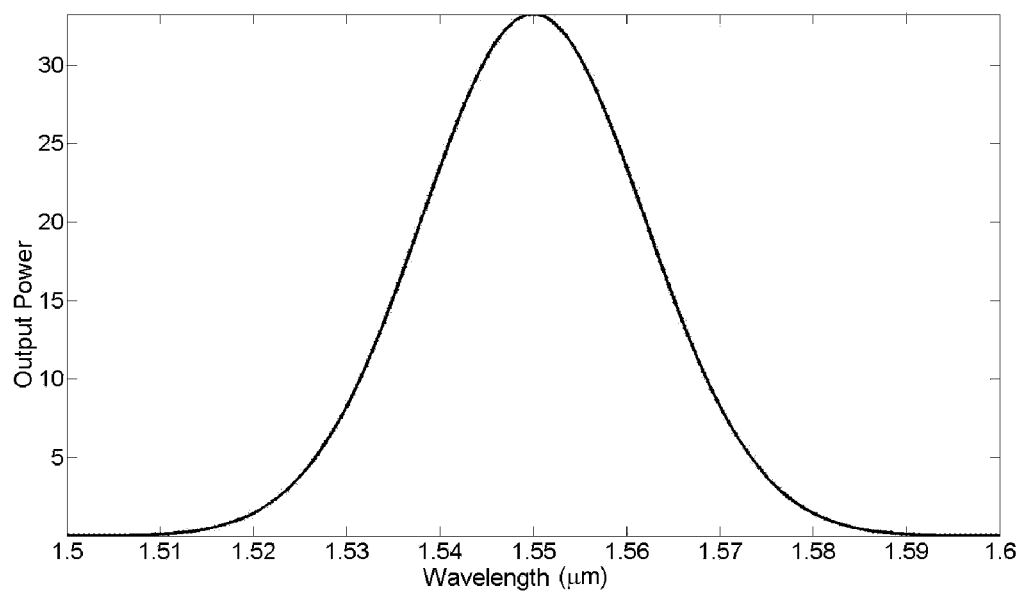
FIG. 13 is a schematic diagram of LED light source spectrum.

Using an LED as the broadband light source whose spectrum is representatively shown in FIG. 13, with the central wavelength at 1550 nm. The envelope function of T shifts when $T_2$ shifts, and the distance between the central wavelength of the envelope function and the central wavelength of the light source at 1550 nm changes, consequently the total output power changes. Therefore, the physical parameter to be measured or the analyte content can be detected by measuring the output power of the total transmitted spectrum.

Consider the same example SOI waveguide used before. The ratios between the change of the mode effective index $n_{eff}$ and the change of the cladding index $n_c$ for TM and TE modes are given in Eq. (5) and Eq. (6), respectively. The cross sections of the waveguides are as shown in FIG. 6. The radii of the two rings are chosen to be 120 μm and 121.2 μm with a difference of 1%. The energy coupling efficiency is set to be 10% and the propagation loss of the waveguide is assumed to be 1 dB/cm. The power of the LED light source is set to be 1 mW.

Figure 14:
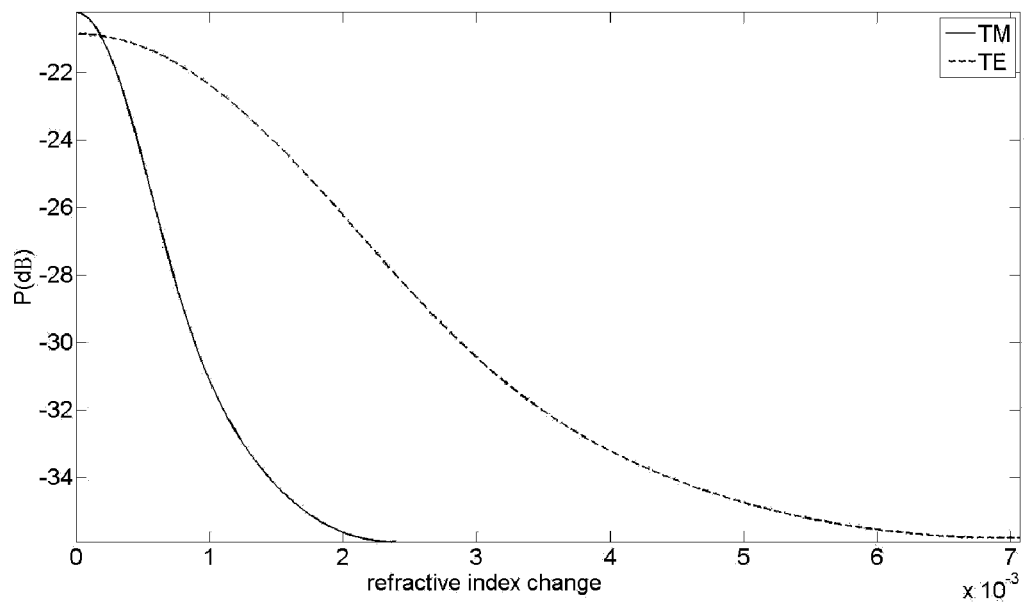
FIG. 14 is the total output power change using TM mode and TE mode in the fourth implementation of the present invention.

FIG. 14 gives the total output power change for TM mode when the refractive index of the analyte changes from 1.33 to $1.33+2.44\times10^{-3}$, and for TE mode when the refractive index of the analyte changes from 1.33 to $1.33+7\times10^{-3}$. As we can see, when the refractive index of the analyte changes ($T_2$ shifts), the total output power decreases because the interval between the central wavelength of the total transmission spectrum T and the central wavelength of the LED light source increases. According to our calculation, the highest sensitivity reaches 15400 dB/RIU for TM mode. Assuming that the power measurement accuracy is 0.01 dB, a refractive index variation as small as $6.5\times10^{-7}$ can be detected. The highest sensitivity for TE mode reaches 4350 dB/RIU, corresponding to a detection limit of the refractive index variation as small as $2.3\times10^{-6}$.

The Fifth Implementation of the Invention

Figure 15:
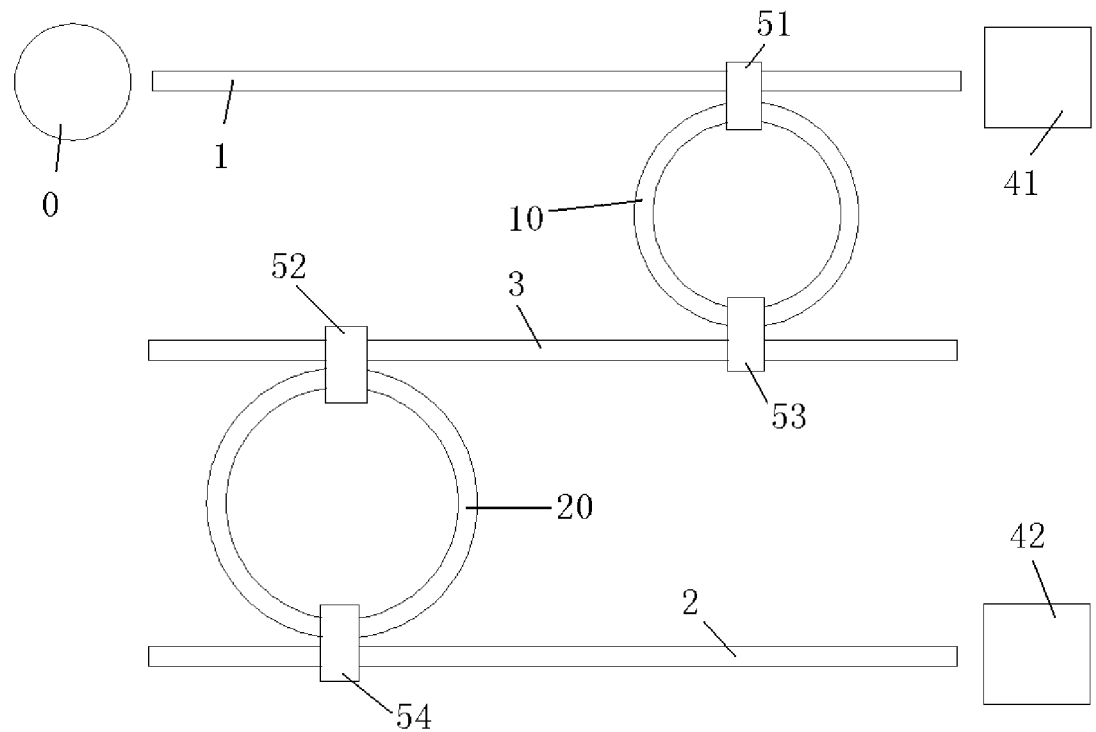
FIG. 15 is a schematic diagram of the fifth implementation of the present invention.

FIG. 15 is the fifth implementation of the present invention. The sensor consists of a broadband light source 0, an input waveguide 1 coupled with the broadband light source 0, a reference ring resonator 10 coupled with the input waveguide, a common bus waveguide 3 coupled with the reference ring resonator 10, a sensing ring resonator 20 coupled with the common bus waveguide 3, an output waveguide 2 coupled with the sensing ring resonator 20, an optical power detector 42 coupled with the output waveguide 2 for measuring the output power. The optical lengths of the reference ring resonator and the sensing ring resonator are different. The resonant frequencies of the reference ring resonator 10 correspond to a series of equally spaced operation frequencies. When one resonant frequency of the sensing ring resonator 20 coincides with one resonant frequency of the reference ring resonator 10, the adjacent resonant peaks are not completely overlapped. At least a portion of the sensing ring resonator 20 is the sensing section (e.g. in the dashed-line rectangle) which is influenced by the physical parameter to be measured such as the stress or temperature, or is in contact with the analyte. The change of the parameter such as the stress or temperature will influence the optical path length of the sensing ring resonator 20. The variation of the refractive index of the analyte can also influence the optical path length of the sensing ring resonator 20 through the evanescent field coupling, consequently inducing a shift of the resonant peaks. The shift is translated to an amplified shift of the envelope function of the total transmission spectrum, due to the Vernier effect of cascaded rings. The displacement between the central wavelength of the total transmission spectrum and the central wavelength of the light source changes, resulting in a change in the total transmitted power. From the output power measured from the output waveguide 2 using power detector 42, the physical parameter to be measured or the analyte information such as the refractive index and concentration can be detected. The power detector 41 is used to measure power from the through-port of the input waveguide 1 (a constant value close to the power of the input light source). The power measure by the detector 42 can be normalized by the power measured from the detector 41 to eliminate the influence of the fluctuation of the input power.

In FIG. 15, the waveguides and ring resonators are coupled by multimode interference couplers 51, 52, 53, and 54.

The implementations above mainly concern the situation when the waveguides and ring resonators are based on planar waveguide. The waveguides and ring resonators can also be based on fibers or nano fibers, and the coupling can be realized by fusing or evanescent field coupling. The fiber has an advantage of polarization-insensitivity.

The Sixth Implementation of the Invention

The ring resonator in the above embodiments is used as an optical filter. It has a high quality factor. The ring resonators can be replaced by other filters such as Mach-Zehnder interferometers or array waveguide gratings or Fabre-Perot interferometers. The Fabre-Perot interferometer can consist of two Bragg gratings.

Figure 16:
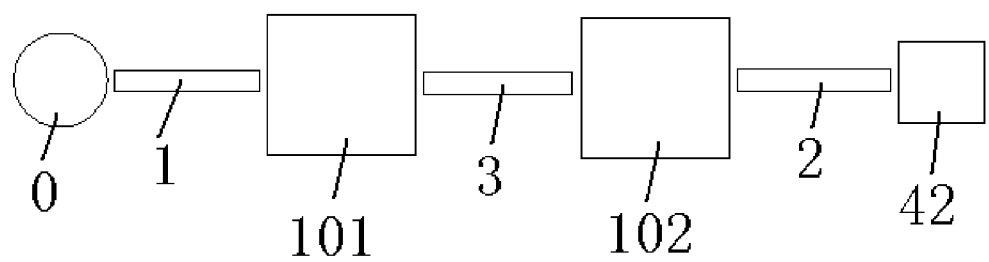
FIG. 16 is a schematic diagram of the sixth implementation of the present invention.

As shown in FIG. 16, the sensor consists of a broadband light source 0, an input waveguide 1 coupled with the broadband light source, a reference optical filter 101 coupled with the input waveguide, a common bus waveguide 3 coupled with the reference optical filter 101, a sensing optical filter 102 coupled with the common bus waveguide 3, an output waveguide 2 coupled with the sensing optical filter 102, an optical power detector 42 used for measuring the output power, the transmission frequencies of the reference optical filter 101 correspond to a series of equally spaced operation frequencies. When one operation frequency of the sensing optical filter 102 coincides with one operation frequency of the reference optical filter 101, the adjacent peaks are not completely overlapped. At least a portion of the sensing optical filter 102 is influenced by the physical parameter to be measured such as the stress or temperature, or is in contact with the analyte. The change of the physical parameter such as the stress or temperature or the change of the refractive index of the analyte will shift the transmission frequencies of the sensing optical filter 102. The frequency shift is translated into an amplified shift of the envelope function of the total transmission spectrum because of the Vernier effect of the cascaded optical filters, resulting in a large displacement between the central wavelength of the total transmission spectrum and the central wavelength of the light source, consequently a large change in the total transmitted power. From the output power measured from the output waveguide 2 using power detector 42, the physical parameter to be measured or the analyte information such as the refractive index and concentration can be detected.

The input waveguide, output waveguide, common bus waveguide, reference optical filter and sensing optical filter are all comprised of fibers or planar integrated waveguides.

The reference optical filter and the sensing optical filter are comprised of one or several Mach-Zehnder interferometers, or array waveguide gratings, or Fabre-Perot interferometers.

The above implementations are only used to illustrate the invention rather than limit the invention. For example, the serial cascade of the two ring resonators can be replaced by parallel connection such that the reference ring resonator 10 and the sensing ring resonator 20 are placed in the two branches of a Mach-Zehnder interferometer and similar functionality can be achieved. Any changes without departing from the spirit and scope of the present invention shall be also regarded as falling into the protection scope of the invention.

What is claimed is:

1. An optical sensor comprising: a broadband light source 0, an input waveguide 1 coupled with the broadband light source 0, a reference ring resonator 10 coupled with the input waveguide, a common bus waveguide 3 coupled with the reference ring resonator 10, a sensing ring resonator 20 coupled with the common bus waveguide 3, an output waveguide 2 coupled with the sensing ring resonator 20, an optical power detector 42 coupled with the output waveguide 2 for measuring the output power; the optical path lengths of said reference ring resonator and sensing ring resonator are substantially the same, the resonant frequencies of said reference ring resonator 10 correspond to a series of equally spaced peaks in its transmission spectrum, the resonant frequencies of said sensing ring resonator 20 substantially coincide with the resonant frequencies of said reference ring resonator 10; at least a portion of the waveguide of the sensing ring resonator 20 is effected by the physical parameter to be measured or is in contact with the analyte while the waveguide of the reference ring resonator 10 is covered by a cladding layer that prevents it from being effected by the physical parameter to be measured or from being in contact with the analyte, the change of the physical parameter to be measured or the analyte causes a shift of the transmission peaks of the sensing ring resonator 20 with respect to those of the reference ring resonator 10, which consequently causes a change of the output power.

2. An optical sensor as defined in claim 1, wherein the waveguides and the ring resonators are coupled by directional couplers or multimode interference couplers.

3. An optical sensor as defined in claim 1, wherein the broadband light source is a light emitting diode.

4. An optical sensor as defined in claim 1, wherein the other end of the input waveguide 1 is coupled with a second optical power detector 41.

5. An optical sensor as defined in claim 1, wherein the physical parameter to be measured is stress or temperature, and the analyte is a liquid or a gas.

6. An optical sensor comprising: a broadband light source 0, an input waveguide 1, a reference optical filter 101, a common bus waveguide 3, an sensing optical filter 102, an output waveguide 2, and an optical power detector 42, which are coupled in sequence; the transmission frequencies of said reference optical filter 101 correspond to a series of equally spaced peaks in its transmission spectrum, the transmission frequencies of said sensing optical filter 102 substantially coincide with the transmission frequencies of said reference optical filter 101; at least a portion of the waveguide of the sensing optical filter 102 is effected by the physical parameter to be measured or is in contact with the analyte while the waveguide of the reference optical filter 101 is covered by a cladding layer that prevents it from being effected by the physical parameter to be measured or from being in contact with the analyte, the change of the physical parameter to be measured or the analyte causes a shift of the transmission peaks of the sensing optical filter 102 with respect to those of the reference optical filter 101, which consequently causes a change of the output power.

7. An optical sensor as defined in claim 6, wherein the waveguides and the optical filters are comprised of fibers or planar integrated waveguides.

8. An optical sensor as defined in claim 6, wherein the optical filters are comprised of one or several Mach-Zehnder interferometers, or array waveguide gratings, or Fabre-Perot interferometers.

9. An optical sensor comprising: a broadband light source 0, an input waveguide 1 coupled with the broadband light source 0, a reference ring resonator 10 coupled with the input waveguide, a common bus waveguide 3 coupled with the reference ring resonator 10, a sensing ring resonator 20 coupled with the common bus waveguide 3, an output waveguide 2 coupled with the sensing ring resonator 20, an optical power detector 42 coupled with the output waveguide 2 for measuring the output power; the optical path lengths of said reference ring resonator and sensing ring resonator are slightly different so that the resonant frequency of said reference ring resonator 10 correspond to a series of equally spaced peaks in its transmission spectrum, and when one resonant frequency of said sensing ring resonator 20 coincides with one resonant frequency of said reference ring resonator 10, the adjacent resonant peaks do not overlap completely; at least a portion of the waveguide of the sensing ring resonator 20 is effected by the physical parameter to be measured or is in contact with the analyte while the waveguide of the reference ring resonator 10 is covered by a cladding layer that prevents it from being effected by the physical parameter to be measured or from being in contact with the analyte, the change of the physical parameter to be measured or the analyte causes a shift of the transmission peaks of the sensing ring resonator 20 with respect to those of the reference ring resonator 10, which consequently causes a change of the output power.

10. An optical sensor as defined in claim 9, wherein the couplers between the input waveguide 1, the common bus waveguide 3 and the reference ring resonator 10 are directional couplers or multimode interference couplers; the couplers between the output waveguide 2, the common bus waveguide 3 and the sensing ring resonator 20 are directional couplers or multimode interference couplers.

11. An optical sensor as defined in claim 9, wherein the broadband light source is a light emitting diode.

12. An optical sensor as defined in claim 9, wherein the other end of the input waveguide 1 is coupled with a second optical power detector 41.

13. An optical sensor as defined in claim 9, wherein the physical parameter to be measured is stress or temperature, and the analyte is a liquid or a gas.

14. An optical sensor comprising: a broadband light source 0, an input waveguide 1, a reference optical filter 101, a common bus waveguide 3, a sensing optical filter 102, an output waveguide 2, an optical power detector 42, which are coupled in sequence; the transmission frequency of said reference optical filter 101 correspond to a series of equally spaced peaks in its transmission spectrum, and when one transmission frequency of said sensing optical filter 102 coincides with one transmission frequency of said reference optical filter 101, the adjacent transmission peaks are not overlapped completely; at least a portion of the waveguide of the sensing optical filter 102 is effected by the physical parameter to be measured or is in contact with the analyte while the waveguide of the reference optical filter 101 is covered by a cladding layer that prevents it from being effected by the physical parameter to be measured or from being in contact with the analyte, the change of the physical parameter to be measured or the analyte causes a shift of the transmission peaks of the sensing optical filter 102 with respect to those of the reference optical filter 101, which consequently causes a change of the output power.

15. An optical sensor as defined in claim 14, wherein the input waveguide 1, the output waveguide 2, the common bus waveguide 3, the reference optical filter 101 and the sensing optical filter 102 are comprised of fibers or planar integrated waveguides.

16. An optical sensor as defined in claim 14, wherein the reference optical filter 101 and sensing optical filter 102 are comprised of one or several Mach-Zehnder interferometers, or array waveguide gratings, or Fabre-Perot interferometers.

* * * * *